United States Patent
Morton et al.

(10) Patent No.: US 8,331,535 B2
(45) Date of Patent: Dec. 11, 2012

(54) GRAPHITE BACKSCATTERED ELECTRON SHIELD FOR USE IN AN X-RAY TUBE

(75) Inventors: Edward James Morton, Guildford (GB); Russell David Luggar, Dorking (GB); Paul De Antonis, Horsham (GB)

(73) Assignee: Rapiscan Systems, Inc., Torrance, CA (US)

( * ) Notice: Subject to any disclaimer, the term of this patent is extended or adjusted under 35 U.S.C. 154(b) by 219 days.

(21) Appl. No.: 12/792,931

(22) Filed: Jun. 3, 2010

(65) Prior Publication Data

US 2011/0007876 A1    Jan. 13, 2011

Related U.S. Application Data

(63) Continuation-in-part of application No. 12/485,897, filed on Jun. 16, 2009, now abandoned, which is a continuation of application No. 10/554,656, filed as application No. PCT/GB2004/001729 on Apr. 23, 2004, now Pat. No. 7,564,939, application No. 12/792,931, which is a continuation-in-part of application No. 12/371,853, filed on Feb. 16, 2009, now Pat. No. 7,903,789, which is a continuation of application No. 10/554,975, filed as application No. PCT/GB2004/001741 on Apr. 23, 2004, now Pat. No. 7,512,215, application No. 12/792,931, which is a continuation-in-part of application No. 12/651,479, filed on Jan. 3, 2010, now abandoned, which is a continuation of application No. 10/554,654, filed as application No. PCT/GB2004/001731 on Apr. 23, 2004, now Pat. No. 7,664,230, application No. 12/792,931, which is a continuation-in-part of application No. 12/364,067, filed on Feb. 2, 2009, now abandoned, which is a continuation of application No.

(Continued)

(30) Foreign Application Priority Data

| Apr. 25, 2003 | (GB) | 0309371.3 |
| Apr. 25, 2003 | (GB) | 0309374.7 |
| Apr. 25, 2003 | (GB) | 0309379.6 |
| Apr. 25, 2003 | (GB) | 0309383.8 |
| Apr. 25, 2003 | (GB) | 0309385.3 |
| Apr. 25, 2003 | (GB) | 0309387.9 |
| Dec. 16, 2005 | (GB) | 0525593.0 |
| Jul. 15, 2008 | (GB) | 0812864.7 |
| Feb. 25, 2009 | (GB) | 0903198.0 |

(51) Int. Cl.
*H01J 5/18* (2006.01)
(52) U.S. Cl. .................... 378/140; 378/143
(58) Field of Classification Search ............. 378/119, 378/121, 124, 140, 143
See application file for complete search history.

(56) References Cited

U.S. PATENT DOCUMENTS 4,171,254 A    10/1979  Koenecke (Continued)

OTHER PUBLICATIONS

PCT Search Report PCT/US10/37167, Dec. 9, 2010, Repiscan Security Products, Inc.

*Primary Examiner* — Courtney Thomas
(74) *Attorney, Agent, or Firm* — Novel IP

(57) ABSTRACT

The present invention is a shielded anode having an anode with a surface facing an electron beam and a shield configured to encompass the anode surface. The shield has at least one aperture and an internal surface facing the anode surface. The shield internal surface and anode surface are separated by a gap in the range of 1 mm to 10 mm. The shield of the present invention is fabricated from a material, such as graphite, that is substantially transmissive to X-ray photons.

16 Claims, 2 Drawing Sheets

Related U.S. Application Data

12/033,035, filed on Feb. 19, 2008, now Pat. No. 7,505,563, which is a continuation of application No. 10/554,569, filed as application No. PCT/GB2004/001732 on Apr. 23, 2004, now Pat. No. 7,349,525, application No. 12/792,931, which is a continuation-in-part of application No. 12/758,764, filed on Apr. 12, 2010, now Pat. No. 7,929,663, which is a continuation of application No. 12/211,219, filed on Sep. 16, 2008, now Pat. No. 7,724,868, which is a continuation of application No. 10/554,655, filed as application No. PCT/GB2004/001751 on Apr. 23, 2004, now Pat. No. 7,440,543, application No. 12/792,931, which is a continuation-in-part of application No. 12/697,073, filed on Jan. 29, 2010, now Pat. No. 8,085,897, which is a continuation of application No. 10/554,570, filed as application No. PCT/GB2004/001747 on Apr. 23, 2004, now Pat. No. 7,684,538, application No. 12/792,931, which is a continuation-in-part of application No. 12/097,422, filed as application No. PCT/GB2006/004684 on Dec. 15, 2006, now Pat. No. 7,876,879, application No. 12/792,931, which is a continuation-in-part of application No. 12/142,005, filed as application No. PCT/GB2006/004684 on Dec. 15, 2006, now Pat. No. 8,135,110, application No. 12/792,931, which is a continuation-in-part of application No. 12/478,757, filed on Jun. 4, 2009, now Pat. No. 8,094,784, which is a continuation of application No. 12/364,067, filed on Feb. 2, 2009, now abandoned, which is a continuation of application No. 12/033,035, filed on Feb. 19, 2008, now Pat. No. 7,505,563, which is a continuation of application No. 10/554,569, filed as application No. PCT/GB2004/001732 on Apr. 23, 2004, now Pat. No. 7,349,525, application No. 12/792,931, which is a continuation-in-part of application No. 12/712,476, filed on Feb. 25, 2010.

(60) Provisional application No. 61/183,591, filed on Jun. 3, 2009, provisional application No. 61/155,572, filed on Feb. 26, 2009.

(56) References Cited

U.S. PATENT DOCUMENTS

| | | |
|---|---|---|
| 4,420,382 A | 12/1983 | Riedl |
| 5,879,807 A | 3/1999 | Inque et al. |
| 2003/0091148 A1 | 5/2003 | Bittner et al. |
| 2004/0022292 A1 | 2/2004 | Morton et al. |
| 2004/0202282 A1* | 10/2004 | Miller ............ 378/140 |
| 2008/0019483 A1 | 1/2008 | Andrews et al. |
| 2009/0159451 A1 | 6/2009 | Tomantschger et al. |
| 2009/0185660 A1 | 7/2009 | Zou et al. |

* cited by examiner

GRAPHITE BACKSCATTERED ELECTRON SHIELD FOR USE IN AN X-RAY TUBE

CROSS-REFERENCE TO RELATED APPLICATIONS

The present application relies on U.S. Patent Provisional Application Ser. No. 61/183,591 filed on Jun. 3, 2009, for priority.

The present application is also a continuation-in-part of U.S. patent application Ser. No. 12/485,897, filed on Jun. 16, 2009 now abandoned, which is a continuation of U.S. patent application Ser. No. 10/554,656, filed on Oct. 25, 2005, and now issued U.S. Pat. No. 7,564,939, which is a 371 national stage application of PCT/GB04/01729, filed on Apr. 23, 2004 and which, in turn, relies on Great Britain Application No. 0309387.9, filed on Apr. 25, 2003, for priority.

The present application is also a continuation-in-part of U.S. patent application Ser. No. 12/371,853, filed on Feb. 16, 2009 now U.S. Pat. No. 7,903,789, which is a continuation of U.S. patent application Ser. No. 10/554,975, filed on Oct. 25, 2005, and now issued U.S. Pat. No. 7,512,215, which is a 371 national stage application of PCT/GB2004/01741, filed on Apr. 23, 2004 and which, in turn, relies on Great Britain Application Number 0309383.8, filed on Apr. 25, 2003, for priority.

The present application is also a continuation-in-part of U.S. patent application Ser. No. 12/651,479, filed on Jan. 3, 2010 now abandoned, which is a continuation of U.S. patent application Ser. No. 10/554,654, filed on Oct. 25, 2005, and now issued U.S. Pat. No. 7,664,230, which is a 371 national stage application of PCT/GB2004/001731, filed on Apr. 23, 2004 and which, in turn, relies on Great Britain Patent Application Number 0309371.3, filed on Apr. 25, 2003, for priority.

The present application is also a continuation-in-part of U.S. patent application Ser. No. 12/364,067, filed on Feb. 2, 2009 now abandoned, which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority.

The present invention is also a continuation-in-part of U.S. patent application Ser. No. 12/758,764, filed on Apr. 12, 2010 now U.S. Pat. No. 7,929,663, which is a continuation of U.S. patent application Ser. No. 12/211,219, filed on Sep. 16, 2008, and now issued U.S. Pat. No. 7,724,868, which is a continuation of U.S. patent Ser. No. 10/554,655, filed on Oct. 25, 2005, and now issued U.S. Pat. No. 7,440,543, which is a 371 national stage application of PCT/GB2004/001751, filed on Apr. 23, 2004, and which, in turn, relies on Great Britain Patent Application Number 0309385.3, filed on Apr. 25, 2003, for priority.

The present application is also a continuation-in-part of U.S. patent application Ser. No. 12/697,073, filed on Jan. 29, 2010 now U.S. Pat. No. 8,085,897, which is a continuation of U.S. patent application Ser. No. 10/554,570, filed on Oct. 25, 2005, and now issued U.S. Pat. No. 7,684,538, which is a 371 national stage application of PCT/GB2004/001747, filed on Apr. 23, 2004, and which, in turn, relies on Great Britain Patent Application Number 0309379.6, filed on Apr. 25, 2003, for priority.

The present application is also a continuation-in-part of U.S. patent application Ser. No. 12/097,422, filed on Jun. 13, 2008 now U.S. Pat. No. 7,876,879, and U.S. patent application Ser. No. 12/142,005, filed on Jun. 19, 2008 now U.S. Pat. No. 8,135,110, both of which are 371 national stage applications of PCT/GB2006/004684, filed on Dec. 15, 2006, which, in turn, relies on Great Britain Patent Application Number 0525593.0, filed on Dec. 16, 2005, for priority.

The present application is also a continuation-in-part of U.S. patent application Ser. No. 12/478,757, filed on Jun. 4, 2009 now U.S. Pat. No. 8,094,784, which is a continuation of U.S. patent application Ser. No. 12/364,067, filed on Feb. 2, 2009 now abandoned, which is a continuation of U.S. patent application Ser. No. 12/033,035, filed on Feb. 19, 2008, and now issued U.S. Pat. No. 7,505,563, which is a continuation of U.S. patent application Ser. No. 10/554,569, filed on Oct. 25, 2005, and now issued U.S. Pat. No. 7,349,525, which is a 371 national stage filing of PCT/GB04/001732, filed on Apr. 23, 2004 and which, in turn, relies on Great Britain Patent Application Number 0309374.7, filed on Apr. 25, 2003, for priority. In addition, U.S. Patent Application number relies on Great Britain Patent Application Number 0812864.7, filed on Jul. 15, 2008, for priority.

The present application is also a continuation-in part of U.S. patent application Ser. No. 12/712,476, filed on Feb. 25, 2010, which relies on U.S. Provisional Patent Application Ser. No. 61/155,572 filed on Feb. 26, 2009 and Great Britain patent application Ser. No. 0903198.0 filed on Feb. 25, 2009, for priority.

Each of the aforementioned PCT, foreign, and U.S. applications, and any applications related thereto, is herein incorporated by reference in their entirety.

FIELD OF THE INVENTION

The present invention relates generally to the field of X-ray tubes. In particular, the present invention relates to a backscattered electron shield for use in an X-ray tube, where the shield is made of graphite.

BACKGROUND OF THE INVENTION

In an X-ray tube, electrons are accelerated from a cathode by an applied voltage and subsequently collide with an anode. During the collision, the electrons interact with the anode and generate X-rays at the point of impact. In addition to X-ray generation, electrons may be backscattered out of the anode back into the X-ray tube vacuum. Up to 50% of the incident electrons may undergo such backscattering. The consequence of this backscattering is that electrical charge can be deposited on surfaces within the tube which, if not dissipated, can result in high voltage instability and potential tube failure.

Thus, what is needed is an apparatus and method for preventing electrons from leaving the anode and entering the X-ray tube vacuum. What is also needed is an apparatus and method for reducing the amount of backscattered electrons leaving the anode area that still allows free access of the incident electrons to the anode and does not impact the resultant X-ray flux.

SUMMARY OF THE INVENTION

In one embodiment, the present invention is directed toward a shielded anode comprising: an anode having a surface facing an electron beam and a shield configured to encompass said surface, wherein said shield has at least one aperture, wherein said shield has an internal surface facing said anode surface, and wherein said shield internal surface and said anode surface are separated by a gap. The gap is in the range of 1 mm to 10 mm, 1 mm to 2 mm, or 5 mm to 10 mm. The shield comprises graphite. The shield is removably attached to said anode. The shield comprises a material that has at least 95% transmission for X-ray photons. The shield comprises a material that has at least 98% transmission for X-ray photons. The shield comprises a material that blocks and absorbs backscattered electrons. The shielded anode further comprises more than one aperture.

In another embodiment, the present invention is directed toward a shielded anode comprising an anode having a length and a surface facing an electron beam; and a shield configured to encompass said surface, wherein said shield has at least one aperture, wherein said shield has an internal surface facing said anode surface, and wherein said shield internal surface and said anode surface are separated by a distance, wherein said distance varies along the length of the anode. The gap is in the range of 1 mm to 10 mm, 1 mm to 2 mm or 5 mm to 10 mm. The shield comprises graphite. The shield is removably attached to said anode. The shield comprises a material that has at least 95% transmission for X-ray photons. The shield comprises a material that has at least 98% transmission for X-ray photons. The shield comprises a material that blocks and absorbs backscattered electrons. The shielded anode further comprises more than one aperture.

BRIEF DESCRIPTION OF THE DRAWINGS

These and other features and advantages of the present invention will be appreciated, as they become better understood by reference to the following detailed description when considered in connection with the accompanying drawings, wherein.

DETAILED DESCRIPTION OF THE INVENTION

The present invention is directed towards an apparatus and method for preventing electrons, generated in an X-ray tube, from leaving an anode and entering the X-ray tube vacuum.

The present invention is also directed towards an apparatus and method for reducing the amount of backscattered electrons leaving the anode area that a) still allows free access of the incident electrons to the anode and b) does not impact the resultant X-ray flux.

In one embodiment, the present invention is directed towards a shield that can be attached to an anode while still allowing free access of incident electrons to the anode, wherein the shield is made of any material that will absorb or repel backscattered electrons while still permitting X-ray photons to pass through.

In one embodiment, the present invention is directed towards a pyrolitic graphite shield that can be attached to an anode while still allowing free access of incident electrons to the anode.

Thus, in one embodiment, the present invention is directed towards an anode shield that has relatively little impact on the resultant X-ray flux and a significant effect on reducing the amount of backscattered electrons leaving the anode area.

In one embodiment, the graphite shield is fixedly attached to the anode. In another embodiment, the graphite shield is removably attached to the anode. In one embodiment, the pyrolitic graphite shield is attached to a linear anode which operates in association with multiple electron sources to produce a scanning X-ray source. In another embodiment, the pyrolitic graphite shield is attached to a linear anode which operates in association with a single source X-ray tube.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

Figure 1:
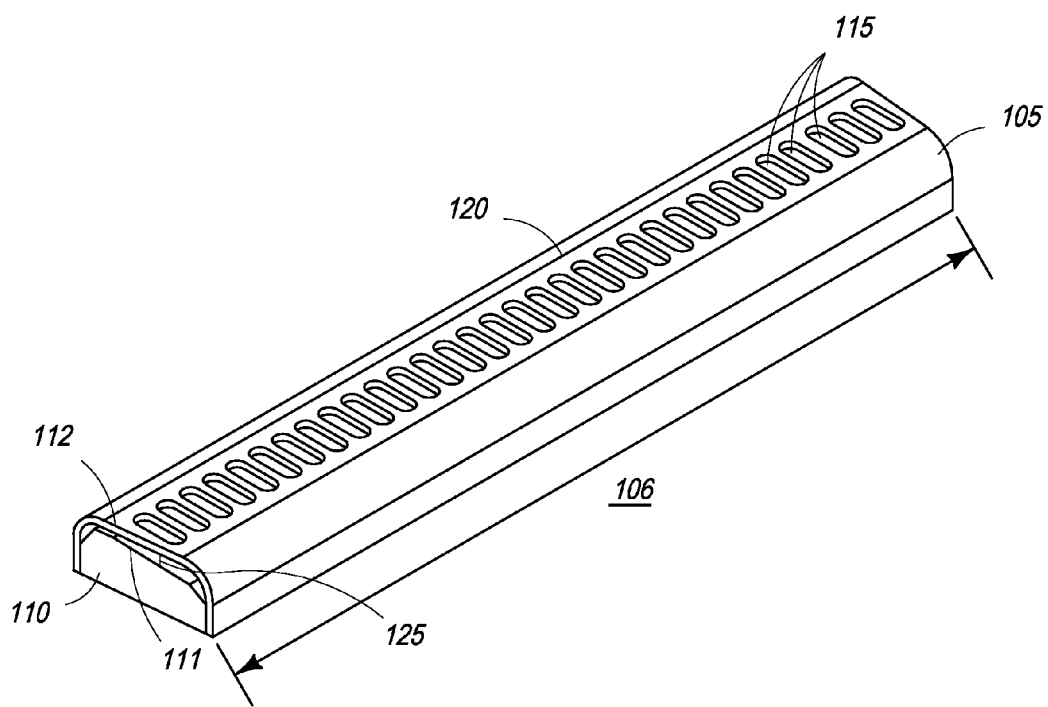
FIG. 1 is an illustration of an electron backscatter shield fitted over a linear multiple target X-ray anode.

FIG. 1 is an illustration of an electron backscatter shield fitted over a linear multiple target X-ray anode. Referring to FIG. 1, a graphite electron backscatter shield 105 is fitted over a linear multiple target X-ray anode 110. In one embodiment, the graphite shield is fixedly attached to the anode. In another embodiment, the graphite shield is removably attached to the anode.

In one embodiment, shield 105 is configured to fit over the linear length 106 of anode 110 and has at least one and preferably multiple apertures 115 cut into and defined by front face 120 to permit free fluence of the incident electron beam. X-rays, generated by the fluence of electrons incident upon the anode 110, pass through the graphite shield 105 essentially unhindered. Backscattered electrons will not be able to pass through the graphite shield 105 and are thus, collected by the shield which, in one embodiment, is electrically coupled to the body of the anode 110.

Figure 2:
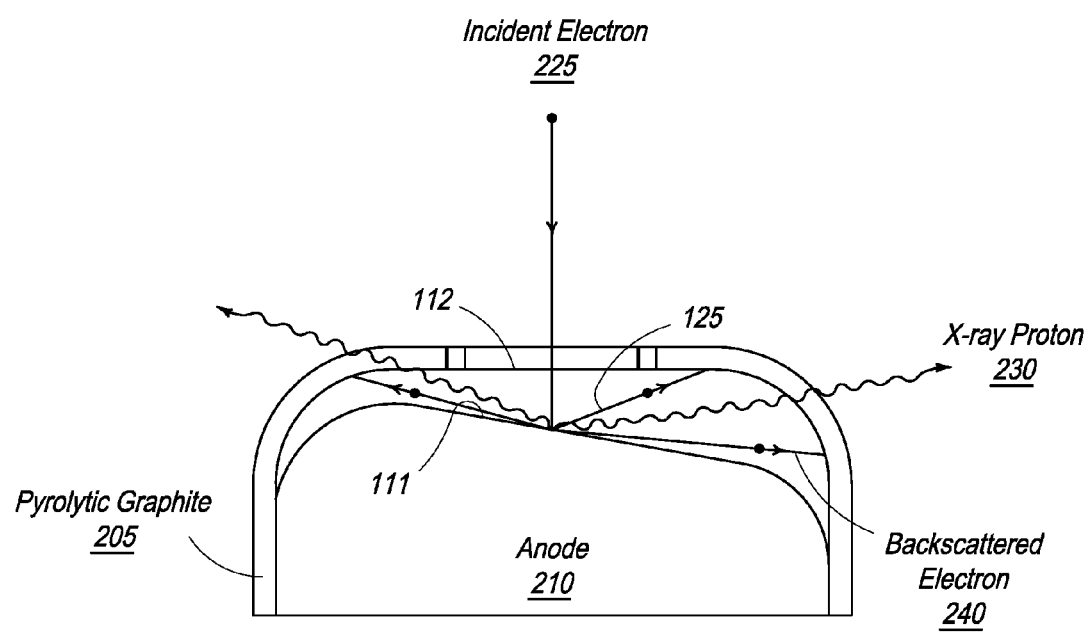
FIG. 2 is a schematic diagram showing the operation of a backscatter electron shield in accordance with the present invention.

In one embodiment, the anode 110 has a surface 111 that faces, and is therefore directly exposed to, the electron beam. In one embodiment, the shield 105 has an internal surface 112 that faces the anode surface 111. In one embodiment, the internal surface 112 and said anode surface 111 are separated by a gap 125. The distance or gap 125 between the surface 111 of anode 110 and internal surface 112 of shield 105 is in the range of 1 mm to 10 mm. In one embodiment, the distance or gap 125 between the surface 111 of anode 110 and internal surface 112 of shield 105 is in the range of 1 mm to 2 mm. In one embodiment, the distance or gap 125 between the surface 111 of anode 110 and internal surface 112 of shield 105 is in the range of 5 mm to 10 mm. FIG. 2 shows distance 125 between the surface 111 of the anode and internal surface 112 of the shield in another view. It should be appreciated that, as shown in FIG. 2, the distance between the internal shield surface and the anode surface varies along the length of the anode surface.

Referring back to FIG. 1, in one embodiment, X-ray generation in the shield 105 (either by incident or backscattered electrons) will be minimized due to the low atomic number (Z) of graphite (Z=6). Electrons that are backscattered directly towards at least one aperture 115 will be able to exit the shield. In one embodiment, electron exit is minimized by standing the shield away from the anode surface and thus reducing the solid angle that the aperture subtends at the X-ray focal spot.

FIG. 2 is a schematic diagram showing the operation of the backscatter electron shield. Anode 210 is covered by electron shield 205, which permits incident electrons 225 to pass unimpeded (and thereby produce X-rays). The shield 205 allows the transmission of X-ray photons through the shield material, but it blocks and absorbs backscattered electrons 240, thereby preventing their entry into the X-ray tube vacuum.

In one embodiment, shield 205 is formed from graphite. Graphite is advantageous in that it will stop backscattered electrons but will neither produce x-rays in the graphite (which would otherwise blur the focal spot and ultimately the image) nor attenuate the x-rays that are produced from the correct part of the anode (focal spot). Electrons with 160 kV energy have a range of 0.25 mm in graphite and therefore a shield 1 mm thick will prevent any electrons passing through the graphite. However, X-ray photon transmission, in one embodiment, for X-ray photons having an energy of 160 kV, is greater than 90%. X-ray photon transmission, in another embodiment, for X-ray photons having an energy of 160 kV, is preferably greater than 95%. X-ray photon transmission, in another embodiment, for X-ray photons having an energy of 160 kV, is preferably at least 98%.

Graphite is electrically conductive and the charge will therefore dissipate to the anode 210. It is also refractory and can withstand any temperature it might reach either during processing or operation. In one embodiment, the shield can be grown onto a former and the apertures laser cut to the required size.

In other embodiments, any material that is electrically conductive and can withstand manufacturing temperature can be employed, including, but not limited to metallic materials such as stainless steel, copper, or titanium. It should be noted herein and understood by those of ordinary skill in the art that considerations for material choice also include cost and manufacturability.

While there has been illustrated and described what is at present considered to be one embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

We claim:

1. A shielded anode comprising: an anode having a surface facing an electron beam and a shield configured to encompass said surface, wherein said shield has at least one aperture, wherein said shield has an internal surface facing said anode surface, wherein said shield internal surface and said anode surface are separated by a gap, and wherein said shield comprises a material that has at least 95% transmission for X-ray photons.

2. The shielded anode of claim 1 wherein said gap is in the range of 1 mm to 10 mm.

3. The shielded anode of claim 1 wherein said gap is in the range of 1 mm to 2 mm.

4. The shielded anode of claim 1 wherein said gap is in the range of 5 mm to 10 mm.

5. The shielded anode of claim 1 wherein said shield comprises a material that has at least 98% transmission for X-ray photons.

6. The shielded anode of claim 1 wherein said shield comprises a material that blocks and absorbs backscattered electrons.

7. The shielded anode of claim 1 further comprising more than one aperture.

8. A shielded anode comprising: an anode having a surface facing an electron beam and a shield configured to encompass said surface, wherein said shield has at least one aperture, wherein said shield has an internal surface facing said anode surface, wherein said shield internal surface and said anode surface are separated by a gap and wherein said shield comprises graphite.

9. A shielded anode comprising: an anode having a length and a surface facing an electron beam; and a shield configured to encompass said surface, wherein said shield has at least one aperture, wherein said shield has an internal surface facing said anode surface, wherein said shield internal surface and said anode surface are separated by a distance, wherein said distance varies along the length of the anode, and wherein said shield comprises a material that has at least 95% transmission for X-ray photons.

10. The shielded anode of claim 9 wherein said gap is in the range of 1 mm to 10 mm.

11. The shielded anode of claim 9 wherein said gap is in the range of 1 mm to 2 mm.

12. The shielded anode of claim 9 wherein said gap is in the range of 5 mm to 10 mm.

13. The shielded anode of claim 9 wherein said shield comprises a material that has at least 98% transmission for X-ray photons.

14. The shielded anode of claim 9 wherein said shield comprises a material that blocks and absorbs backscattered electrons.

15. The shielded anode of claim 9 further comprising more than one aperture.

16. A shielded anode comprising: an anode having a length and a surface facing an electron beam; and a shield configured to encompass said surface, wherein said shield has at least one aperture, wherein said shield has an internal surface facing said anode surface, wherein said shield internal surface and said anode surface are separated by a distance, wherein said distance varies along the length of the anode, and wherein said shield comprises graphite.

* * * * *